US 6,188,923 B1

(12) United States Patent
Bechtold

(10) Patent No.: US 6,188,923 B1
(45) Date of Patent: Feb. 13, 2001

(54) METHOD AND APPARATUS FOR LOCAL HEATING AND GLOBAL MONITORING OF A TISSUE

(75) Inventor: Mario Bechtold, Röttenbach (DE)

(73) Assignee: Siemens Aktiengesellschaft, Munich (DE)

( * ) Notice: Under 35 U.S.C. 154(b), the term of this patent shall be extended for 0 days.

(21) Appl. No.: 09/160,876

(22) Filed: Sep. 25, 1998

(30) Foreign Application Priority Data

Sep. 30, 1997 (DE) ............................................... 197 43 294

(51) Int. Cl.[7] ....................................................... A61B 6/00
(52) U.S. Cl. ............................... 600/427; 600/412; 601/3
(58) Field of Search ............................... 600/427, 411, 600/549, 412; 601/2, 3

(56) References Cited

U.S. PATENT DOCUMENTS 5,323,779 * 6/1994 Hardy et al. .
5,443,068 * 8/1995 Cline et al. .
5,509,418 * 4/1996 Lum et al. .
5,526,814 * 6/1996 Cline et al. .

* cited by examiner

Primary Examiner—Marvin M. Lateef
Assistant Examiner—Shawna J. Shaw
(74) Attorney, Agent, or Firm—Herbert L. Lerner; Laurence A. Greenberg; Werner H. Stemer

(57) ABSTRACT

A method and an apparatus for local heating and global monitoring of a tissue disposed in an imaging device, monitored by the imaging device and substantially simultaneously heated by focused ultrasound from an appropriate source. The ultrasound is generated outside the imaging device and is guided to the tissue through the use of a waveguide. In particular, the imaging device is a magnetic resonance scanner.

25 Claims, 2 Drawing Sheets

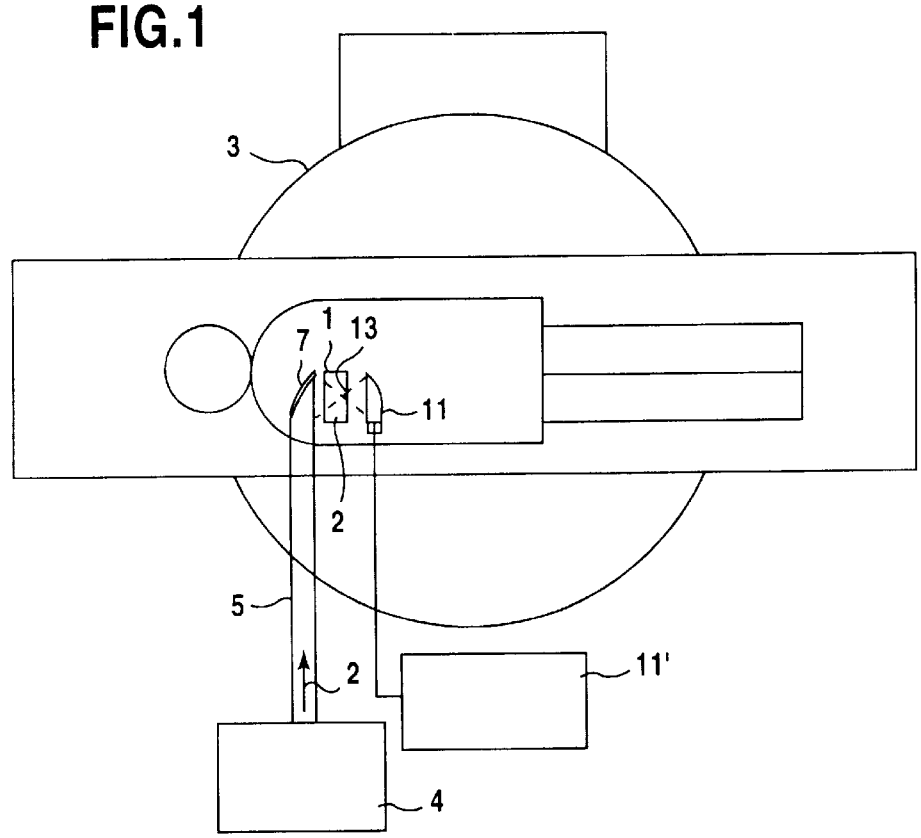
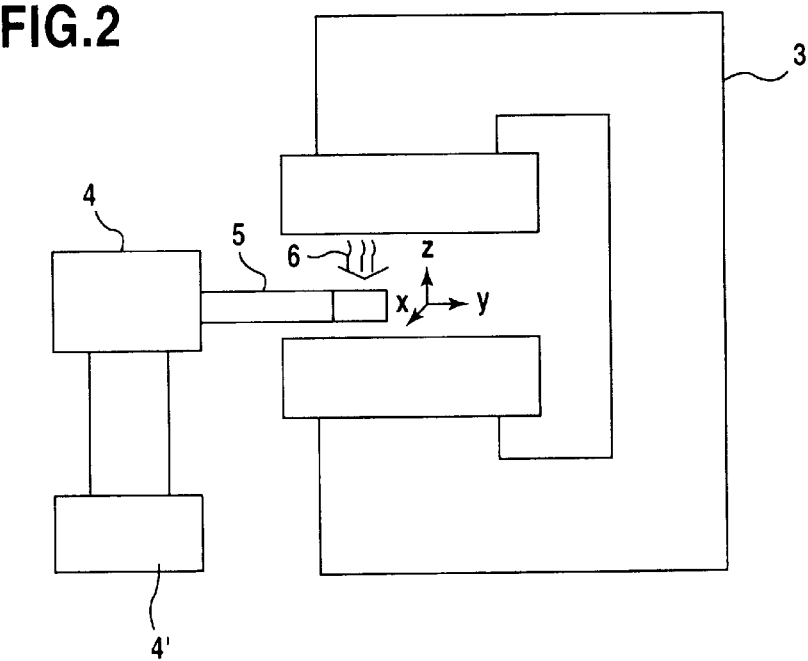

METHOD AND APPARATUS FOR LOCAL HEATING AND GLOBAL MONITORING OF A TISSUE

BACKGROUND OF THE INVENTION

Field of the Invention

The invention relates to a method for local heating and global monitoring of a tissue disposed in an imaging device, monitored by the imaging device and heated substantially simultaneously by focused ultrasound. The invention also relates to an apparatus for local heating and global monitoring of a tissue, including an imaging device for receiving the tissue and monitoring the tissue, as well as a source for generating ultrasound.

The invention relates in particular to a method and an apparatus for treating and in particular destroying a selected zone within a tissue in the human body. The tissue is heated for a sufficient length of time, by focusing ultrasound, to a comparatively high temperature sufficient to kill the tissue. The focus of the ultrasound, that is the region in which the energy of the ultrasound attains sufficiently high intensity, is typically approximately 3 mm in diameter and approximately 10 mm in length. If there is a need to treat a larger zone of tissue, then the zone can be divided up into an appropriate grid and treated appropriately by variable focusing of the ultrasound. Both the monitoring of the temperature attained in the zone, and the distribution of that temperature, are of major importance. It is especially critical to prevent the destruction of healthy tissue located immediately adjacent diseased and especially tumorous tissue. Efforts are therefore made to monitor the temperature distribution in a tissue treated with focused ultrasound.

A magnetic resonance scanner with a support for a patient who is to be treated and with a source for focused ultrasound built into the patient support, is sold by the General Electric Company. In that apparatus, complicated provisions for electromagnetic shielding are necessary, in order to prevent the source from impeding the operation of the magnetic resonance scanner itself. A complicated safeguard to protect the patient to be treated against electric currents from the source is also provided.

A paper entitled "Temperature Monitoring of Focused Ultrasound Therapy by MRI", by P. Huber, in Ultrasonics Symposium 1994, pages 1825 ff., describes a combination of a source for focused ultrasound and a magnetic resonance scanner, in which the source and the magnetic resonance scanner are operated in alternation. The magnetic resonance scanner is set up in such a way that it can detect and display both the location of the focus and the temperature distribution in the tissue being treated.

Fundamental information on temperature measurement through the use of magnetic resonance imaging using a contrast medium is found in a paper entitled "Non-Invasive In Vivo Temperature Mapping of Ultrasound Heating using Magnetic Resonance Techniques", by N. B. Smith, in Ultrasonics Symposium 1994, pages 1829 ff.

SUMMARY OF THE INVENTION

It is accordingly an object of the invention to provide a method and an apparatus for local heating and global monitoring of a tissue, which overcome the hereinaforementioned disadvantages of the heretofore-known methods and apparatuses of this general type and in which treatment of a tissue by ultrasound with substantially simultaneous monitoring by an imaging device can be performed without interference and without the possibility of unintended damage to the tissue.

With the foregoing and other objects in view there is provided, in accordance with the invention, a method for local heating and global monitoring of a tissue, which comprises placing a tissue in an imaging device; monitoring the tissue with the imaging device; and substantially simultaneously heating the tissue with focused ultrasound generated outside the imaging device and guided to the tissue by a waveguide.

Accordingly, along the lines of the invention, the close connection between the source for the ultrasound and the imaging device that was always required previously has been done away with. All that is required for introducing the ultrasound, required for treating the tissue, into the tissue is a waveguide. Any electronic circuit for generating the ultrasound, which at least when it is intended to suit the purposes discussed at the outset must include a power amplifier for furnishing relatively high-power ultrasound, and which would thus be fundamentally quite capable of causing extensive electromagnetic interference, can be disposed away from the imaging device and shielded off in every respect. Only the waveguide is in close spatial contact with the imaging device. This waveguide must pass only acoustical and not, for instance, electromagnetic signals into the imaging device, and thus it is not itself an independent source of electromagnetic interference. In particular, the waveguide may be constructed as an electrical insulator.

In accordance with another mode of the invention, the imaging device operates with at least one electromagnetic field at an associated operating frequency, the ultrasound has an associated ultrasonic frequency, and the at least one operating frequency is different from every integral multiple of the ultrasonic frequency. It is thus assured that because of the distinction between the operating frequency and the ultrasonic frequency and its integral multiples, largely interference-free operation of the imaging device is assured. Thus the spatial distancing between the imaging device and the source is augmented with functionally dictated distancing, since the possibility of electromagnetic influence on the imaging device from the source is reduced even further.

In accordance with a further mode of the invention, a power level at which the ultrasound heats the tissue is measured. This measurement can be performed with known measuring instruments of various kinds. In particular, a thermooptical measuring instrument can be employed. In this measuring instrument, the energy of the ultrasound is converted into heat in a corresponding absorber and is measured as a temperature through the use of a fiber optic sensor. This offers an additional opportunity for monitoring the effect of the ultrasound, thus making the method substantially safer in use.

In accordance with an added mode of the invention, the ultrasound has chronologically variable focusing. Therefore, the spatial location of the area in the tissue that is particularly affected by the ultrasound can be shifted, thus making a relatively large zone in the tissue accessible to the ultrasonic heating.

In accordance with an additional mode of the invention, the imaging device operates through the use of magnetic resonance imaging. Magnetic resonance imaging is an especially gentle method for treating a tissue and is thus especially well suited for use within the context of medicine.

In accordance with yet another mode of the invention, a magnetic resonance imaging method is employed in which monitoring of the temperature distribution in the tissue is possible, making the consequences of the treatment with ultrasound immediately detectable. In particular, the monitoring of the temperature distribution can be carried out on the basis of a contrast medium introduced into the tissue beforehand.

In accordance with yet a further mode of the invention, the local heating or thermal treatment and the global monitoring of the tissue are performed jointly and simultaneously. To that end, the invention provides a favorable precondition for avoiding mutual influence between the imaging device and the source.

In accordance with yet an added mode of the invention, the tissue is heated through the use of the ultrasound locally to a temperature between 60° C. and 90° C. This allows the use of the method to destroy a diseased and in particular tumorous area in living tissue. A major contribution to this capability is the possibility that the effect of the ultrasound on the treated tissue can be monitored immediately in chronological terms. This is because the tissue can be monitored globally, that is over an area having a comparatively small part which is a zone to be treated with the ultrasound. This thus allows drawing an unambiguous and preferably quantitative conclusion about the temperature increase in the tissue that is due to the ultrasound.

With the objects of the invention in view there is also provided an apparatus for local heating and global monitoring of a tissue, comprising an imaging device for receiving and monitoring a tissue; a source disposed outside the imaging device for generating ultrasound; an acoustical waveguide for conducting the ultrasound from the source into the imaging device; and a focuser for focusing the ultrasound.

In accordance with another feature of the invention, the waveguide is formed of glass. In particular, such a waveguide can be a rod of quartz glass, for example.

In accordance with a further feature of the invention, the waveguide is provided in the form of a glass fiber configuration, and it is also preferred that this waveguide be provided with a horn on each end. Such a horn on an end of the waveguide oriented toward the source reduces the cross section of an ultrasonic beam originating at the source, which allows the provision of an especially compact, and optionally flexible, glass fiber configuration. A horn on the end of this waveguide oriented toward the tissue widens the cross section of the ultrasonic beam originating at the source, and thus makes it possible for the beam to enter the tissue with a correspondingly large cross section and correspondingly less action. This contributes to preventing undesired influence on the tissue outside the zone that is meant to be treated with the ultrasound. This in turn is of major value in conjunction with a medical use of the apparatus.

In accordance with an added feature of the invention, the waveguide is in the form of a tube, in particular formed of a ceramic, that is filled with a liquid. In particular, water can be considered as the liquid.

In accordance with an additional feature of the invention, the focuser includes a lens or mirror in particular, which is preferably adjustable.

In accordance with yet another feature of the invention, the imaging device is a magnetic resonance scanner, as already noted in conjunction with the method of the invention.

In accordance with yet a further feature of the invention, the focuser is provided with markings that can be detected by the imaging device. With the aid of the imaging device, it can be estimated how the ultrasound passes through the tissue, and thus the zone in the tissue that is finally treated can be determined with certainty. This feature, too, is of major importance for using the apparatus in the medical field for destroying diseased, in particular tumorous, tissue. This refinement enables narrowly demarcating the tissue to be destroyed, and thus avoiding undesired damage to healthy tissue when killing diseased tissue.

In accordance with yet an added feature of the invention, there is provided a measuring instrument for measuring a power level at which the ultrasound heats the tissue. Details of this feature have already been discussed in terms of a step of the method of the invention.

In accordance with a concomitant feature of the invention, preferred applications of the apparatus that pertain in particular to specific setups of the apparatus are treatment of tissue in the human breast or in the human abdomen. In the latter case, consideration may be given to the male prostate as a possible site for treatment utilizing the invention.

Other features which are considered as characteristic for the invention are set forth in the appended claims.

Although the invention is illustrated and described herein as embodied in a method and an apparatus for local heating and global monitoring of a tissue, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIGS. 1 and 2 are respective diagrammatic plan and elevational views of an exemplary embodiment of an apparatus for local heating and global monitoring of a tissue.

DESCRIPTION OF THE PREFERRED EMBODIMENTS

Figure 3:
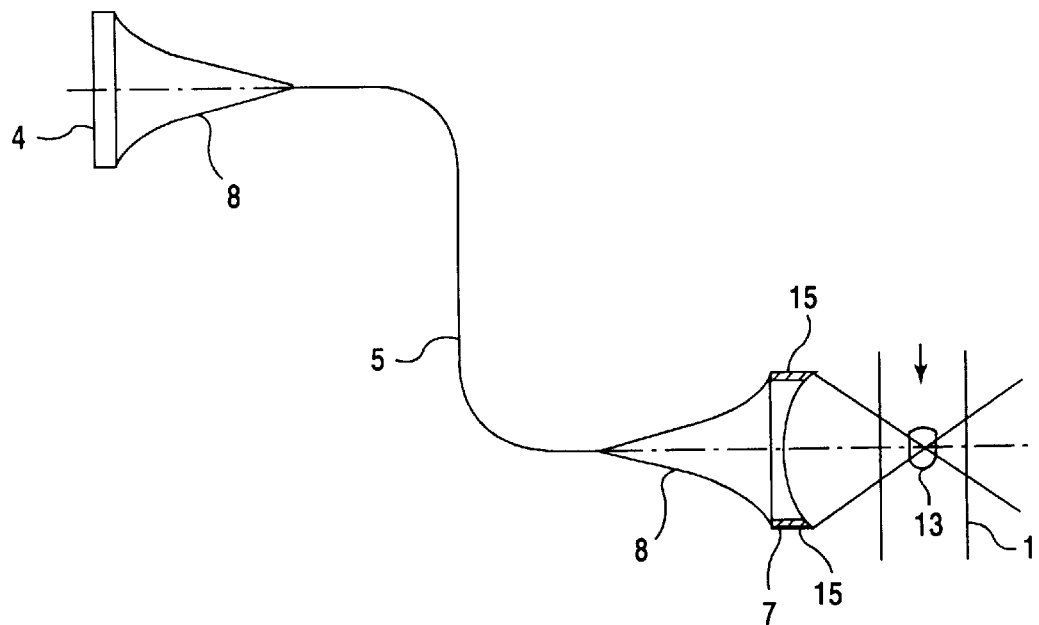
FIGS. 3 and 4 are respective elevational and sectional views of exemplary embodiments of waveguides that can be employed in connection with the invention.

Referring now to the figures of the drawings in detail and first, particularly, to FIG. 1 thereof, there is seen a diagrammatic view of an apparatus for treating a tissue 1 through the use of ultrasound 2, including an imaging device 3, or more concretely a magnetic resonance scanner, and a source 4 for ultrasound 2, with an energy supply 4'. This view is shown in a direction extending vertically from top to bottom in the conventional sense. FIG. 2 shows this same apparatus, seen in a conventionally horizontal direction. These two drawing figures will now be discussed jointly.

A special waveguide 5 is provided in order to conduct the ultrasound 2 from the source 4 into the imaging device 3 and the tissue 1 to be treated. In the present case this waveguide 2 may be a rod of quartz glass, for example. The source 4 furnishes the ultrasound 2 at a certain ultrasonic frequency. In order to treat the tissue 1 in the manner referred to repeatedly above, that is in which portions of the tissue 1 are to be killed, the ultrasonic frequency is typically above 1 MHz. The imaging device 3 also employs electromagnetic fields 6 at certain operating frequencies, as professionals in this field are well aware. The operating frequency and the ultrasonic frequency are each selected in such a way that the operating frequency is different from every integral multiple of the ultrasonic frequency. In this way, influence on the imaging device 3 by the source 4 is kept as slight as possible.

A focuser 7, which in the present case is a mirror mounted on the waveguide 5, is provided in order to focus the ultrasound 2 into the tissue 1. This focuser 7 assures that the energy of the ultrasound is focused within a very spatially limited focus 13, and thus effects relatively major heating of the tissue 1 in the area of this focus 13. A measuring instrument 11 is provided in order to determine the energy that has been converted into heat in the focus 13. The measuring instrument 11 measures the power level of the ultrasound 2 that emerges from the tissue 1. The energy deposited in the area of the focus 13 is thus the difference between the energy furnished by the source 4, which still has to be determined by a suitable measuring instrument, and the energy measured by the measuring instrument 11. As a result, the apparatus can be manipulated safely and reliably.

FIG. 3 shows an exemplary embodiment of the waveguide 5. The waveguide 5 is formed of a glass fiber configuration and is provided, together with an evalution/display unit 11' with a horn 8 on each end. The horn 8 disposed on the end of the waveguide 5 facing toward the source 4 (shown symbolically as an ultrasound transducer) serves to concentrate the energy, supplied by the source 4, in the small cross section of the waveguide 5. The horn 8 disposed on the end of the waveguide 5 facing toward the tissue 1 serves to distribute the energy of the ultrasound 2 over a large cross section again, enabling the ultrasound 2 to enter the tissue 1 to be treated over a comparatively large cross section. The focuser 7 is a lens provided for focusing the ultrasound 2. This lens concentrates the energy of the ultrasound within a comparatively small area around the focus 13 and causes a major temperature increase there. This is utilized in particular for killing the tissue 1 in the vicinity of the focus 13.

Figure 4:
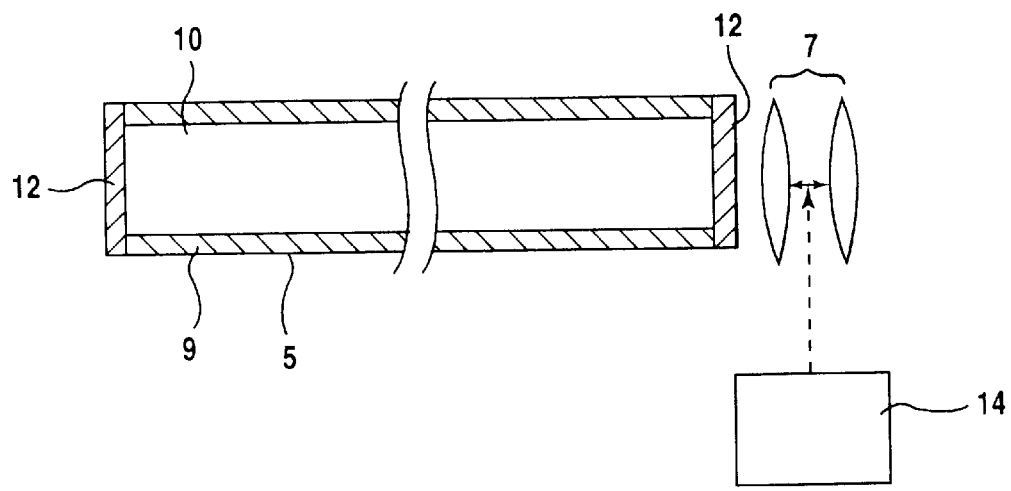

FIG. 4 shows a further feature of the waveguide 5. The waveguide includes a tube 9, which is formed of a suitable ceramic, is filled with a liquid 10, specifically water, and is closed with two windows 12. The focuser 7, which is also shown, in this case includes two lenses that can be displaced relative to one another (as is indicated by a double-headed arrow) and an associated actuating device 14.

The invention relates to a method and an apparatus for locally heating and globally monitoring a tissue. The invention enables genuine chronologically coincident local heating, through the use of focused ultrasound, and global monitoring, in particular through the use of magnetic resonance imaging. Mutual influence between the source for the ultrasound and the imaging device for the monitoring is avoided, and possible damage to the tissue to be treated from the source, or electric lines leading to it, and the like is precluded. The invention is especially well suited to medical use, in particular within the context of tumor therapy in the human female breast or the human male prostate.

I claim:

1. A method for local heating and global monitoring of a tissue, which comprises:
   placing a tissue in an imaging device;
   monitoring the tissue with the imaging device; and
   substantially simultaneously heating the tissue with focused ultrasound generated outside the imaging device and guided to the tissue by a waveguide.

2. The method according to claim 1, which comprises operating the imaging device with at least one electromagnetic field at an associated operating frequency; the ultrasound having an associated ultrasonic frequency; and the at least one operating frequency differing from every integral multiple of the ultrasonic frequency.

3. The method according to claim 1, which comprises measuring a power level at which the ultrasound heats the tissue.

4. The method according to claim 1, which comprises chronologically variably focusing the ultrasound.

5. The method according to claim 1, which comprises operating the imaging device by magnetic resonance imaging.

6. The method according to claim 1, which comprises monitoring a temperature distribution in the tissue with the imaging device.

7. The method according to claim 1, which comprises monitoring a temperature distribution in the tissue with the imaging device on the basis of a contrast medium introduced into the tissue beforehand.

8. The method according to claim 1, which comprises performing the heating and the monitoring steps jointly and simultaneously.

9. The method according to claim 1, which comprises locally heating the tissue by the ultrasound to a temperature between 60° C. and 90° C.

10. An apparatus for local heating and global monitoring of a tissue, comprising:
    an imaging device for receiving and monitoring a tissue;
    a source disposed outside said imaging device for generating ultrasound;
    an acoustical waveguide for conducting the ultrasound from said source into said imaging device; and
    a focuser for focusing the ultrasound.

11. The apparatus according to claim 10, wherein said acoustical waveguide is formed of glass.

12. The apparatus according to claim 10, wherein said acoustical waveguide is formed of quartz glass.

13. The apparatus according to claim 10, wherein said waveguide is a glass fiber configuration.

14. The apparatus according to claim 13, wherein said waveguide has ends, and horns are each disposed at a respective one of said ends.

15. The apparatus according to claim 10, wherein said waveguide is a tube filled with a liquid.

16. The apparatus according to claim 15, wherein said tube is formed of a ceramic and said liquid is water.

17. The apparatus according to claim 10, wherein said focuser is a lens.

18. The apparatus according to claim 17, wherein said lens is adjustable.

19. The apparatus according to claim 10, wherein said focuser is a mirror.

20. The apparatus according to claim 18, wherein said mirror is adjustable.

21. The apparatus according to claim 10, wherein said imaging device is a magnetic resonance scanner.

22. The apparatus according to claim 10, wherein said focuser has markings to be picked up by said imaging device.

23. The apparatus according to claim 10, including a measuring instrument for measuring a power level at which the ultrasound heats the tissue.

24. The apparatus according to claim 10, wherein said imaging device is adapted to monitor the tissue in a human female breast.

25. The apparatus according to claim 10, wherein said imaging device is adapted to monitor the tissue in a human abdomen.

* * * * *